United States Patent [19]

Carter et al.

[11] Patent Number: 4,508,832
[45] Date of Patent: Apr. 2, 1985

[54] ELLIPSOMETRICALLY MEASURING RATE OF OPTICAL CHANGE IN IMMUNOASSAY

[75] Inventors: Timothy J. N. Carter, Geneva; Claus Dähne, Onex, both of Switzerland

[73] Assignee: Battelle Memorial Institute, Carouge, Switzerland

[21] Appl. No.: 389,973

[22] Filed: Jun. 18, 1982

[30] Foreign Application Priority Data

Jun. 22, 1981 [EP] European Pat. Off. ...... 81 81 0255.0

[51] Int. Cl.³ .................... G01N 33/54; G01N 21/17; G01N 21/21
[52] U.S. Cl. .................... 436/517; 356/246; 356/364; 436/527; 436/805
[58] Field of Search .............. 436/517, 805

[56] References Cited

U.S. PATENT DOCUMENTS 2,666,355 1/1954 Trurnit .
3,979,184 9/1976 Glaever .
4,050,895 9/1977 Hardy .
4,054,646 10/1977 Glaever .................... 436/805 X

FOREIGN PATENT DOCUMENTS 2301824 9/1976 France .

OTHER PUBLICATIONS

W. E. J. Neal et al., Journal of Physics & Scientific Instruments, 6, 409-416 (1973).
P. A. Cuypers et al., Anal. Biochem., 84, 56-67 (1978).
R. M. A. Azzam et al., Phys. Med. Biol., 22(3), 422-430 (1977).
Rothen, A. et al., Helvetica Chimica Acta., 54(4), 1208-1216 (1971).

Primary Examiner—Sidney Marantz
Attorney, Agent, or Firm—Karl F. Ross; Herbert Dubno

[57] ABSTRACT

A layer of bioactive molecules is coated on a dielectric substrate and is contacted with a solution to be analyzed containing a complex conjugate of said molecule. The rate of complexion of said conjugate moiety with the layer which is a function of its concentration in the analyte is measured by optical means and correlated with corresponding rates obtained from standard reference measurements, thus providing data for determining the unknown concentration of said conjugate moiety in the solution to be analyzed.

6 Claims, 11 Drawing Figures

ELLIPSOMETRICALLY MEASURING RATE OF OPTICAL CHANGE IN IMMUNOASSAY

FIELD OF THE INVENTION

The present invention relates to bioassays or immunoassays, i.e. to methods for determining bioactive substances in samples. Such assays are useful in fields such as the bio-sciences, medicine, agriculture and the like.

BACKGROUND OF THE INVENTION

In general, bioassays or immunoassays are based on the reaction of a bioactive substance (commonly referred to as the "antigen" $A_G$) with a specific complex conjugate thereof (commonly referred to as the "antibody" $A_B$), whereby a complex molecule $A_G A_B$ is formed and the amount of $A_G$ (or, vice-versa, $A_B$) is measured by various techniques. These techniques belong to two broadly classified groups of methods: the methods involving using an excess of reagent ($A_B$) and measuring said excess after reaction completion and the methods called the "limited reagent" or "saturation assay" methods (see, for instance, "Radioimmunoassay and Related Procedures in Medicine", Proceedings of a Symposium, Berlin 1977, Vol 1, p. 247 and followings). Briefly summarized, "saturation assays" involve the use of a system in which the test substance or analyte (containing the antigen to be measured) is treated with a limited amount of a specific reagent to give the analyte/reagent complex plus some residual analyte. Yet, prior to the reaction, a known amount of labelled antigen is added to the sample to be tested so that the proportion of the labelled antigen ($A_G^*$) to the unlabelled one (unknown) remains the same in said residual analyte as it was at the start. Since the known amount of $A_B$ used will bind a known amount of the $A_{G+}A_G^*$ mixture it suffices to determine the residual $A_G^*$ (by means of its label) to calculate the amount of $A_G$ originally present in the sample. To give an example, suppose that the sample contains x equivalents of an enzyme ($A_G$) to be measured by means of a known amount (g) of a specific enzyme antibody to this ($A_B$) that forms an $A_G A_B$ complex (with, for instance, a 1:1 molecular ratio of both components). Then, prior to the reaction, a equivalents of the same enzyme to be measured but in labelled form ($A_G^*$) are added to the sample. Thus, in the course of the reaction, a portion of g equivalents of antigen ($A_G + A_G^*$) is consumed by the g equivalents of antibody. Now, after removing the complex from the mixture, the residual $A_G^*$ is ascertained by conventional means. If it is found, by substracting the value measured for the remaining $A_G^*$, that the amount actually consumed was b equivalents, it becomes evident, since $A_G$ and $A_G^*$ are chemically indentical and consumed at the same rate, that the ratio of consumed $A_G^*$ to consumed $A_G$, i.e. b/g-b should be equal to the original ratio a/x, from which x=[a(g-b)]/b can be easily calculated. Obviously, the antibody ($A_B$) and antigen ($A_G$) can be replaced by any other bonding pairs such as avidin-biotin or vitamin B12-intrinsic factor and members of these conjugate pairs may be determined in an analogous fashion to these described herein. (Exhaustive description of the general features of bioassays in the sense of the present invention can be found in the following references U.S. Pat. No. 4,256,834 and 4,238,565.)

The aforesaid method is quite attractive but however suffers from several drawbacks: First, it requires that the substance to be ascertained be available in pure labelled form, for instance in radioactive form or with other labelling groups (color generating groups, fluorescent groups, specifically chemically reactive groups or light scattering particles). Such labelled compounds may be chemically unstable or short lived (for instance $I^{131}$ labelled compounds have a half-life of only 3 months). Second, the test requires that the complex $A_G A_B$ be isolated in pure form (whether the activity of the labelled portion be measured on the complex itself or in the residual mixture) and such separation may be tedious and expensive. Third, labelled $A_G^*$ may have, depending on the type of labelling (e.g. by additional groups), a reactivity that may slightly differ from the non-labelled $A_G$ (at least regarding that reaction involving the formation of the analytical complex sought) which is a source of errors in the measurements.

Hence, ideally, a test for achieving the above purpose should simultaneously be specific, sensitive, give inherently accurate results, work under homogeneous conditions and involve storage stable reagents. Consequently, labelling is fundamentally undesirable and a test involving no such labelled reagents should desirably be made available. Such kinds of test already exist based on the experimental fact that, in some case, the $A_B$ and $A_G$ having each more than one reactive site, they tend to form aggregates that will eventually provide light scattering or absorbing effects. Such effects can be measured by conventional nephelometric or colorimetric techniques but, in general, the tests lack sensitivity. The present invention remedies such drawbacks. It comprises contacting with the sample to be determined a substrate the surface of which is, at least partly, coated with a film of or containing $A_B$ (or $A_G$) distributed on the surface of said substrate, measuring the rate of optical change involved as the result of the reaction of $A_B$ (or $A_G$) and the $A_G$ (or $A_B$) of the sample, then correlating the rate curve thus obtained with standard rate curves from identical measurements done with standard samples of $A_G$ (or $A_B$). Preferably, the optical changes to be measured are those occurring when reflection takes place at the boundary between substrate and film.

By correlating the standard curves with the experimental curves, the desired results about the amount of $A_G$ (or $A_B$) in the analytical sample can be easily determined according to usual means. For instance, the curves can be compared visually and the results are extrapolated therefrom or the calculation can be done by a computer, standard data being stored in the memory thereof. Thus, if the rate curves are recorded by some automatic measuring and recording equipment, the rate data can be automatically fed to such a computer connected to the equipment and the results can be immediately displayed on a display instrument (meter, digital display or chart recorder). Appropriate analysis of the rate data obtained allows the discrimination of the required reaction between the $A_G$ and $A_B$ from other reactions proceeding at a faster or slower rate and provides a measurement in a shorter time than the same reaction proceeding to equilibrium. In other words, rate curves may be the result of two or more simultaneous processes, the individual rates of which may be distinguished from the slopes of various suitable segments constituting the overall curves. General treatment of complex rate curves is known per se (see for instance, C. P. PRICE & K. SPENCER, Centrifugal Analyzers in Clinical Chemistry, Praeger Scientific (1980), p. 159–169).

In the present invention, the optical changes occuring during the immunoassay reaction involved are preferably monitored by ellipsometry. Although other monitoring techniques may be visualized (see for instance U.S. Pat. No. 4,050,895), ellipsometry has been found, as far, a very sensitive and reliable means for determining the optical changes due to the reaction of the antibody coated surface with the antigen containing sample (see for instance French Pat. No. 2.301.824). Although the exact nature of the complex forming reaction of $A_B$ plus $A_G$ on the film has not been particularly investigated in all cases where the present method is applicable (and actually does not need to be so to provide useful results), it is thought that the said changes in the film are related to thickness and/or refraction index modifications. This is very likely since, indeed, the reaction of the coated $A_B$ and the $A_G$ of the sample logically leads to the conversion of the $A_B$ coating into an $A_B A_G$ complex coating. Thus, ellipsometry is particularly suited in the case.

In order for the reader to better understand how the present invention is implemented practically, some elementary principles of ellipsometry will be briefly reviewed hereinbelow with the help of the accompanying drawing.

FURTHER BACKGROUND

Figure 1:
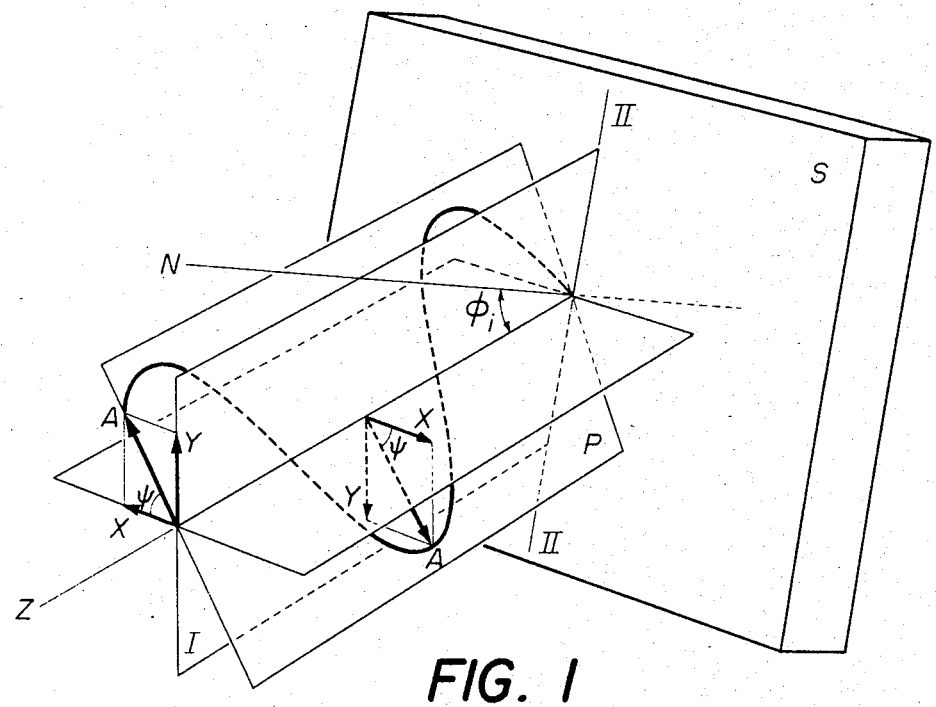
FIG. 1 is a schematic illustration showing how a beam of polarized light can be represented by two rectangular vectors in a right-angle coordinates system oriented by an angle $\psi$ relative to said beam the latter falling on a reflecting surface S with an angle of incidence $\phi_i$.

The principles of ellipsometry can be briefly summarized as follows: the amplitude vector A of any beam of plane polarized light, i.e. light vibrating transversally to the direction Z but within the plane of progapation P (see FIG. 1) can actually be considered equivalent to the vector sum of two right angle vectors directed perpendicular to said direction of propagation Z. This is illustrated on FIG. 1 in which A is the amplitude vector of the polarized light and X and Y are its right angle components in a system of arbitrarily oriented coordinates. The chosen orientation angle $\psi$, i.e. the angle between A and X is called the azimuth angle and the criteria for selecting the correct value for $\psi$ will be given below. The plane I is defined as the plane of incidence of the beam and Y is its parallel (p) component (within the plane of incidence) and X is its "senkrecht" (perpendicular or "s") component. Now, when the beam in the P plane falls on the surface of a slab S, the geometry may always be arranged ($\psi$ can be properly selected) for having the plane I coincide with the plane formed by Z and the straight line N perpendicular to S at the point of incidence. Under such conditions, the remaining characterizing factor of the system is the angle of incidence $\phi_i$ between Z and N. If S is a transparent dielectric layer (see FIG. 2) with refractive index $n_2$ surrounded by transparent media with indexes, respectively $n_1$ and $n_3$, smaller than $n_2$ ($n_1$ and $n_3$ may actually be the same as in the case of S being a glass plate in air) and $\phi_i$ is varied from 0° to $\pi/2$, the following happens in theory to the externally and internally reflected beams, Rex and Rin, respectively (Fresnel laws): If $\phi_i$ is small both the $X_i$ and $Y_i$ are reflected and refracted to some extent (the X component is shown as a dot on FIG. 2 since the plane I coincides with the plane of the paper). In the reflected ray Rex, $X_{Rex}$ is phase shifted by $\pi$ relative to $X_i$ but this is not so for $Y_{Rex}$. If $\phi_i$ is increased to the value $\phi$ where the angle between Rex and the refracted beam is 90°, ($\phi_i$=the Brewster angle) the $Y_{Rex}$ component (the parallel component) vanishes. When $\phi_i$ exceeds the Brewster angle, both the external reflected components $X_{Rex}$ and $Y_{Rex}$ are present again but both are now shifted by $\pi$ relative to the incident components.

Figure 2:
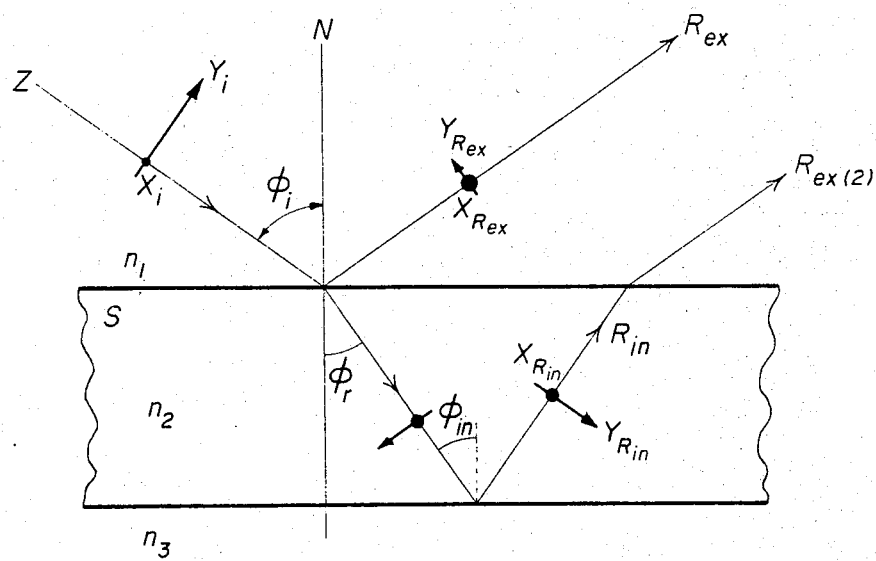
FIG. 2 is a side sectional view along line II—II of FIG. 1, tilted about 90° to the right, showing schematically the changes occurring to the reflected light components in the case of a dielectric reflecting slab at an incidence angle $\phi_i$ near the Brewster angle $\phi$.

FIG. 2 represents a situation close to the Brewster angle, i.e. $X_{Rex}$ is pictured as a strong dot and $Y_{Rex}$ as a very short arrow. In view of Stokes relations, exactly the reverse will happen to the internally reflected light up to an angle $\phi_c$ (larger than the Brewster angle) beyond which total reflection occurs. What then happens to the totally reflected beam Rin will be discussed later. Depending on the embodiments, the present invention is concerned with external reflexion, with internal reflexion, or by combinations of both effects as will be described in details hereinafter.

Figure 3:
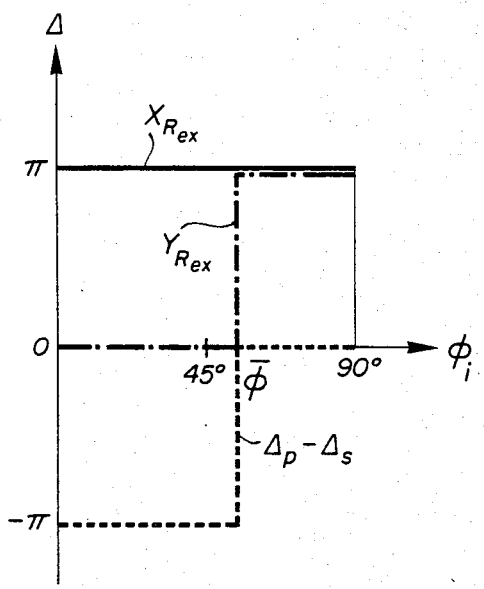
FIG. 3 is a graph that shows the phase shift undergone by the parallel (p) $Y_{Rex}$ and perpendicular (s) $X_{Rex}$ vectors during reflection as a funtion of $\phi_i$ and the difference of these phase shifts.

FIG. 3 illustrates the phase shifts $\Delta$ to which the externally reflected components $X_{Rex}$ and $Y_{Rex}$ are theoretically subjected when the surface of S is the interface between rare and dense dielectrics (as in FIG. 2). In FIG. 3 also, the dotted line represents the phase shift difference ($\Delta_p - \Delta_s$) relative to the parallel component $Y_{Rex}$ and the senkrecht component $X_{Rex}$. It is this difference which is the key factor in ellipsometry as will be seen below.

Figure 4:
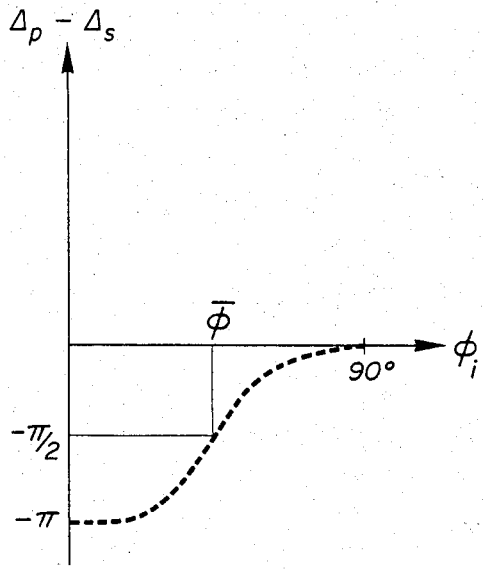
FIG. 4 is a graph similar to that of FIG. 3 but showing the variation of the phase shift difference in the case where the reflecting surface is a film coated dielectric or a metal surface.

Now, the above considerations about phase shifts differences being either zero or $\pi$, i.e. leading to plane polarized reflected light, do not hold if the reflecting surface is coated with a film of foreign material or if the surface is a metallic surface or both. In such cases the $\Delta_p - \Delta_s$ curve is rounded off as shown in FIG. 4 which is not referring to any particular practical case but only displayed for illustration. Thus, in such types of cases, the reflected X and Y vectors will be phase-shifted by some values different from zero or $\pi$ and the vector sum will become an ellipse unless, of course, the difference is $\pi/2$ in which case the $A_R$ reflected vector will still be a straight line but tilted 90° (this is the same as when visualizing a sinusoidal signal on an oscilloscope with a sine base line of the same frequency but out of phase by any angle). The theory of such phenomena was developed by DRUDE around 1890 (see for instance Ellipsometry in the Measurement of Surfaces and Thin Films, Symposium Proceedings, Washington 1963, Editors: E. PASSAGLIA et al). Ellipsometry based measurement techniques precisely measure the changes of ellipticity brought up by the presence of films (or other surface modifications, e.g. corrosion) on reflecting surfaces. Such measurements are extremely sensitive as tiny film variations (a few Å) produce quite significant changes in the elliptical parameters of the elliptically polarized light and these can be measured in terms of angles (phase angle differences and azimuths). The techniques usually involve starting with a beam of polarized light applied to the sample with a known azimuth angle ($\psi$). The reflected elliptically (in general) polarized light from the sample is phased in again by means of a compensating $\pi/4$ phase retardation device (for instance a plate of birefringent material) appropriately rotated (angle of ellipticity) for restoring a plane polarized beam and the resulting azimuth of this beam is determined by crossing with an analyzer, for instance a Nicol prism, up to an angle of maximum extinction.

SUMMARY OF THE INVENTION

The present invention operates on the same principles but with variations introducing quite interesting and unexpected advantages. In the invention a metallic or dielectric supporting substrate, usually a flat surface, is coated with a layer of antibody (it is to be remembered that the term antibody $A_B$ is used here in a very general fashion, i.e. it means any conjugate to a bioactive molecule that one wishes to analyze: an enzyme, a hormone, a virus, a bioactive peptide in general, a vaccine, etc. . . .). In general, one prefers dielectric surfaces like glass or some synthetic resins like cellophane since they have a good inherent affinity for bioactive molecules (of course, in case they have not, the surface can be made bonding by special treatments known in the art such as grafting bonding sites, applying an intermediate reactive layer, etc. . . .). The coating can be done by usual means, e.g. dipping the substrate into a solution of $A_B$ and leaving it there until $A_B$ attaches to the plate as a uniform layer and thereafter draining, rinsing with pure water and allowing to stand under storage conditions (dry or moist depending on the nature of the antibody). Then, the surface is immersed into a suitable reaction medium (e.g. an aqueous buffer) and placed at the correct angle on the path of the incident beam of polarized light; the test sample is then added to the medium, whereby the desired reaction occurs between the analyte and the coated surface and the elliptical parameter changes of the light reflected from the surface are measured with time, wherefrom the desired rate curve is provided.

In the invention, advantage is taken from the external reflected light (the case when a metallic surface is used or when a dielectric plate is coated on one side only) or from a combination of the externally and internally reflected light (the case when a thin plate of glass or other transparent material is coated on both sides) and the angle of incidence $\phi_i$ is below the angle for total internal reflection, or from multiple internal reflection as will be seen hereinafter when discussing the devices for carrying out the invention. In the prior art presently known to the inventors, there exists a few references dealing with the study of $A_G/A_B$ type reactions occurring on surfaces. Said references are: A. ROTHEN, Ellipsometric Studies of Thin Films: Progress in Surface & Membrane Science 8 (1974), 81-118. R. B. DAVIS et al, Ellipsometric Observations of Surface Adsorption and Molecular Interactions of Native and Modified Fibrinogen and Factor VIII: Surface Science 96 (1980), 539-554. R. M. A. AZZAM et al, Kinetics of Protein Adsorption and Immunological Reactions at a Liquid/Solid Interface by Ellipsometry: Phys. Med. Biol. 22 (1977) 422-430. A. ROTHEN et al, Serological Reactions of Protein Films and Denatured Proteins: J. Experimental Medicine 76 (1942), 437-450. P. A. CUYPERS et al, Ellipsometry as a Tool to Study Protein Films at Liquid/Solid Interfaces: Analytical Biochemistry 84 (1978), 56-67. In some of these references, there are described the reactions of bioactive molecules on surfaces coated with specific complexing conjugates, such reactions being studied by ellipsometry. However, none of these references appear to suggest that such techniques can be applied to immunoassays by reference to standard rate curves like in the present invention.

Figure 5A:
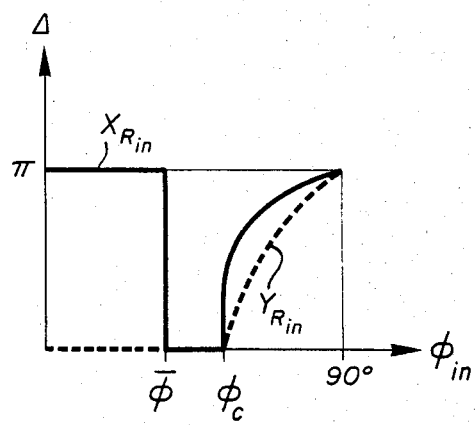
FIGS. 5A and 5B are graphs showing the phase shifts undergone by the internally reflected light components.
Figure 5B:
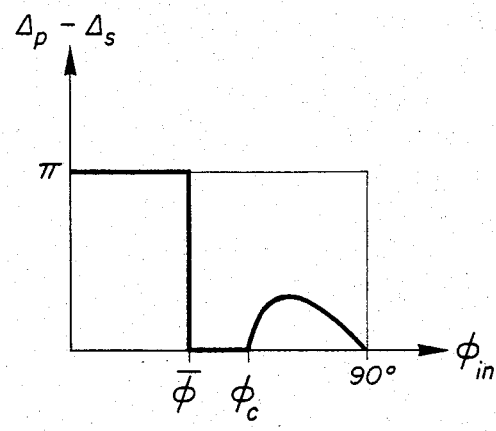

Also, in none of the references known until now has there been any report of simultaneously studying surface changes occurring on both sides of a dielectric plate. And this is here one of the key advantages of the present invention. For better understanding this, we shall return to the internally reflected beam Rin (see FIG. 2) and see how the "p" ($Y_{Rin}$) and "s" ($X_{Rin}$) components are shifted from each other. This, which typically exemplifies reflection at the boundary from an optically dense to a rare medium is also described by the Fresnel equations (see, for instance, M. BORN, Optik, J. Springer, Berlin (1933) and is illustrated by the scheme on FIG. 5. In FIG. 5A, the phase shifts as a function of the angle of incidence are graphically indicated for both the parallel and the senkrecht components. Up to the critical angle $\phi_c$ (i.e. the angle beyond which there will be total reflection in the plate), the shifts are $\pi$ or zero therefore the differences (see FIG. 5B) are also $\pi$ or zero which means that for a plane polarized Rin beam the "p" and "s" components will be in phase and the addition vector will still be a straight line. Beyond $\phi_c$ and up to the grazing angle ($\phi = 90°$), the $\Delta_p - \Delta_s$ is the humped curve shown; hence the "p" and the "s" components will be shifted from each other by any angle and ellipticity will result.

Therefore, one of the embodiments of the present invention precisely relies on the total reflection case and, more particularly, to multiple reflection within the plate, the ellipticity generating parameters being governed by the changes occuring outside the dielectric plate, i.e. being related to the growth of an $A_BA_G$ film on both sides of said plate. It will be shown hereinafter how this condition is embodied practically in the invention but it must be emphasized by now that the present inventors have also discovered that the situation in which the angle of incidence is smaller than $\phi_c$ can also lead to a practical embodiment of the present invention. In other words, it has been shown that, the secondary externally reflected beam (see FIG. 2) being also elliptically polarized when the rearside of the plate is film coated, it amplifies the output signal reflected by the sample instead of interfering destructively (as would be expected). This element of surprise further adds to the originality of the invention. The set up for embodying this aspect of the invention will be disclosed hereinafter.

The instrument used for carrying out the bioassay method of the present invention essentially comprises a cell for holding the reaction medium and enabling the reaction to take place i.e. the sample to be analyzed and the substrate coated with a bioactive surface, a source of polarized light, means for directing a beam of said polarized light with predetermined azimuths and incidence angles on said substrate and means for measuring the changes in the elliptical parameter of the light reflected from the substrate by either the rear-side or both rear-side and front side thereof or, after multiple reflection, within the substrate.

SPECIFIC DESCRIPTION

Figure 6:
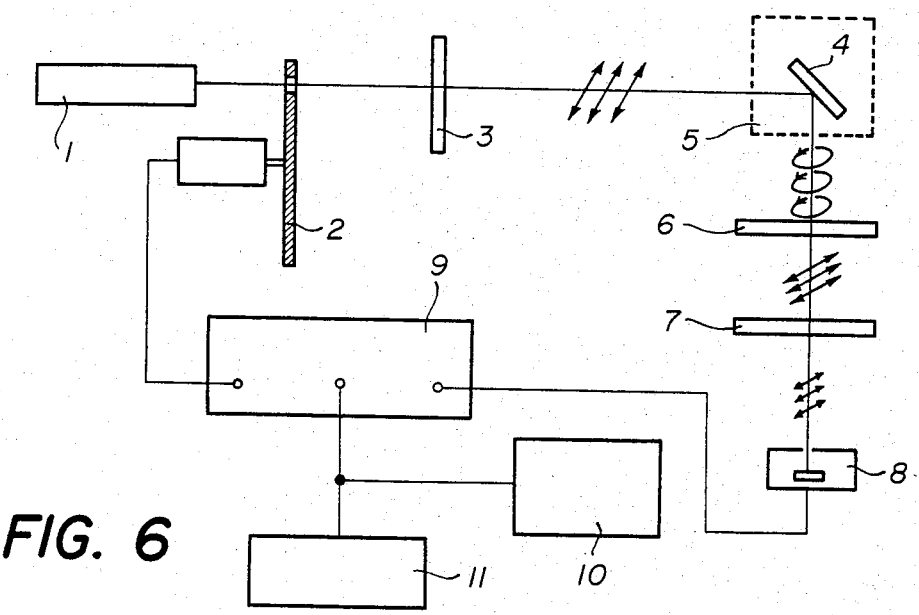
FIG. 6 is a general schematic representation of an automatic recording ellipsometer applied to the measurement of changes occurring on the surface of an antibody coated substrate in contact with a test sample containing an antigen.

The ellipsometer installation shown in FIG. 6 comprises first a light source 1 which is a He-Ne laser in this embodiment (5 mW at $\lambda=632,8$ nm) but which could be any source suitable for use in ellipsometry. The source used in the present example provides visible light, but of course sources providing energy outside the visible (i.e. UV or IR radiations) can also be used. Generally, radiations from about $2.10^2$ to $2.10^4$ nm can be used. Examples of sources in this range are laser lights such as He-Ne ($\lambda=632.8$ nm), Ar ($\lambda=488$ nm, 514.5 nm and other wavelengths), Kr ($\lambda=647.1$ nm and other wavelengths). Other sources such as incandescent lamp with monochromator and mercury arc with narrow-band filter centered on some of the prominent lines in the Hg discharge spectrum can also be used. Then the installation comprises, in the path of the light from the source 1, a chopper 2 for providing a periodically interrupted signal (the chopper also provides a reference signal at the same frequency the use of which is described later), a polarizer 3 for providing a beam of plane polarized light with adjustable azimuth angle $\psi$. Usually the polarizer 3 is a Nicol prism (but it could be any other polarizing means commonly used in this connection such as a Glan-Thompson prism) and the $\psi$ angle is usually set up at 45° (but this is purely optional and other values for $\psi$ could be selected if found convenient). Then, the plane polarized beam falls on the sample reflecting element or substrate 4 (one of the simplest embodiments of which is shown on FIG. 7) located in a sample holding space 5. The light reflected from the sample is now elliptically polarized and goes across a compensator 6 for converting it again into a plane polarized beam. The compensator is usually a $\pi/2$ wave plate, i.e. a plate made of a birefringent material cut parallel to the optic axis. In such case, if the elliptically polarized beam crosses normally to the plate there is no side refraction of the ordinary and the extraordinary rays and if the plate is further turned to have its optic axis parallel to the axis of the ellipse, the perpendicular $X_{Rex}$ and parallel $Y_{Rex}$ vectors will be put back in phase and the ellipse will reduce to a straight line making an angle (azimuth of the reflected beam) with the line of reference. Then, the installation further comprises another polarizer means, the analyzer 7, which enables, by appropriate rotation, to minimize the signal (and give a value for the $\psi$ of reflection). Incidentally, the angle to which the compensator is turned is a measure of the ellipticity of the elliptically polarized light (hence of the $\Delta$ phase lag). Now, the installation still comprises a light detector 8 for converting the light signal into an electric signal which is fed to a lock-in amplifier 9. The lock-in amplifier operates upon the reference signal from the chopper 2 to give phase sensitive detection enabling a great reduction in background noise. Of course, if desired, the chopped light signal could be replaced by a pulsed signal from a light emitting diode or a diode laser. Then the signal from the amplifier 9 is sent to a signal-processing unit 11 which contains a microprocessor where rate data are memorized and correlation between standard data and test data are computerized. For a more qualitative judgement of the measurement a chart recorder 10 connected to amplifier 9 is used.

Briefly summarized, the present ellipsometer installation operates as follows:

once the various optical components have been properly adjusted for intensity and focusing, the sample holder cell (to be described later) together with the substrate coated with the $A_B$ or $A_B$ containing film is filled with the medium for carrying out the reaction (e.g. buffer). The compensator 6 and the analyzer 7 are alternately adjusted until a minimal signal is obtained from the detector. Then, after ensuring that no drift is present, the test sample is added and rapidly mixed with the reaction medium whereby the reaction starts with consecutive progressive changes in the ellipsometric parameters of the set-up. These changes, i.e the signals from the detector are monitored for some time and the response curve recorded on the display 10 and processed in the computer unit 11.

Figure 7:
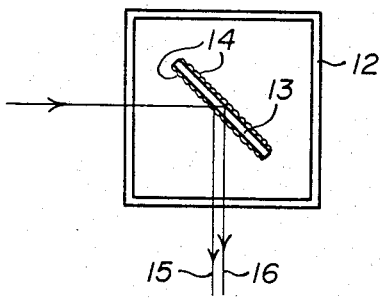
FIG. 7 is an enlarged schematic view of a detail of the instrument of FIG. 6, i.e. a cuvette for undertaking the bioassay to be monitored.

One of the embodiments of the sample analysing element is shown on FIG. 7. It comprises a cuvette 12 (usually made of optical glass, having negligible birefringence) for enclosing the reaction medium and a dielectric plate 13 (glass or any other transparent material such as Lucite, Plexiglass, acrylics, polysulfones, polycarbonate, polystyrene, polyvinylchloride and the like or minerals such as calcite, germanium, silicon, fluorine, carnallite, NaCl, gallium arsenide or quartz crystals can be used) coated on both sides with an antibody containing film 14. The polarized light strikes the plate 13 at an angle of incidence in the vicinity of the Brewster angle (i.e. 40°–55°) and the reflected elliptically polarized light emerges in the form of two beams 15 and 16 of externally and internally reflected light. When the plate 13 is thin enough, i.e. of the order of several hundred $\mu$, (e.g. 100–500$\mu$) the beams 15 and 16 are very near to each other and can be processed together without any particular focusing problem. The output of the two beams add together instead of cancelling out each other to some degree which is unexpected. The advantage of this embodiment is, of course, the production of a higher signal level which increases the sensitivity of the test; however, one drawback is the variation in optical signal due to turbulences as the light travels through the fluid reaction medium.

Figure 8:
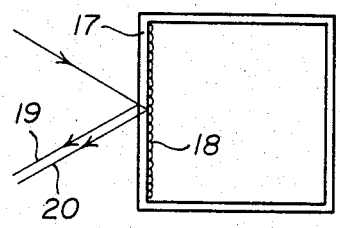
FIG. 8 is a modification of the cuvette of FIG. 7.

In a second embodiment shown on FIG. 8, the sample analyzing outfit is also a cuvette 17 and the substrate on which the $A_B$ or $A_B$ containing film 18 is deposited is one of the inside walls of the cuvette itself. There, the reflected light emerges also in the form of two beams 19 and 20 but only the internally reflected beam 20 is elliptically polarized due to the presence of the film 18, and this being in spite of having an incidence angle (on the back-side) below the critical angle of total reflection, which is one of the surprising features of the present invention. This embodiment will minimize time dependent losses incurred in the previous embodiment but the sensitivity is further reduced because of the energy loss consecutive to the formation of the beam 19.

Figure 9:
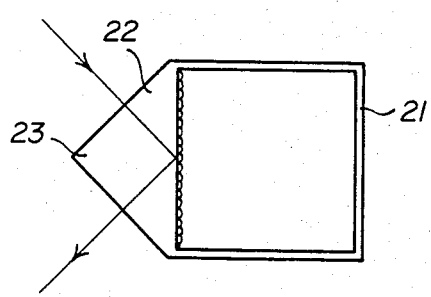
FIG. 9 is a cuvette with another embodiment of substrate coated with a reactive film.

Such a drawback is eliminated in the modification shown on FIG. 9 which comprises also a cuvette 21 but the external side of one of the walls thereof is cut in the form of a prism 22. The angles of the prism are such that the incident and reflected rays will cross the prism sides at right angles. Thus the front angle 23 of the prism will be equal to $2\phi_i$. This will permit minimizing the disturbing loss due to the front reflected beam.

In one modification of the embodiment of FIG. 9, a separate prism is provided and glued to the external side of the wall of the cell bearing the $A_G$ coating by means of an adhesive, the refraction index of which matches as much as possible with the refraction indexes of the prism and the cell walls. In this manner the losses by reflexion at the prism/cell interface can be minimized.

Figure 10:
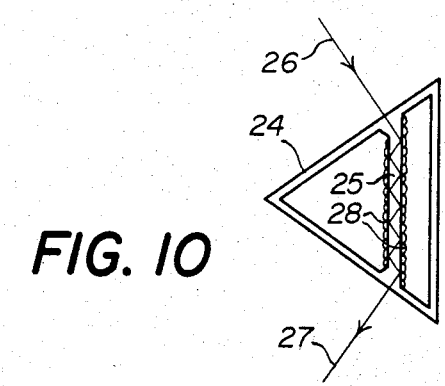
FIG. 10 is similar to FIG. 9 but with a differently cut substrate and operated at a different angle of incidence $\phi_i$ enabling total reflection within the substrate.

In a further embodiment pictured schematically in FIG. 10 (seen from above, as in the other previous figures), the cell 24 has the shape indicated with an inside plate member 25 not extending to the bottom thereof. The angles of the cell are arranged for having the incident light beam 26 to undergo multiple reflection within plate 25 before being reflected out as shown by the arrow 27. The sides of plate 25 are coated with the antibody prior to the reaction (as usual) and the test solution is introduced into the cell whereby film (28) modification will take place on both sides of member 25 and, due to the multiple reflection at the plate 25/film/sample solution boundary, the resulting ellipticity producing effects will be amplified at each successive reflection site. The utmost sensitivity in the method of the invention can be attained by this embodiment since with using a plate 25 sufficiently long and sufficiently thin (e.g. 30-40 mm long and 10-100μ thick) a number of successive reflections of the order of $10^3$ or more can be obtained. With such an arrangement, solutions of antigen with concentrations in the range of a few μg/l can be measured.

It is worth noting that for carrying out the method of the invention, no particular calculations of the $\psi$ and $\Delta$ values by the Drude formulae are necessary because only rate data (comparative measurements) are needed. Of course, in special cases of investigation, the present method is also perfectly usable for gaining deeper insight regarding the exact nature, the thickness and the index of refraction of the coatings before and after reacting with the complexing conjugate, using then the classical ellipsometry equations. It should also be kept in mind that the ellipsometric installation described hereinbefore for illustrative purposes is not the only arrangement of suitable optical elements for implementing the method of the invention. Thus, for instance, in a simple modification, the compensator 6 could be installed in front of the sample (instead of being placed after) thus producing elliptically polarized beam that would then be phased-in due to to reflection by the sample.

In an improved modification of the aforesaid ellipsometric installation, the signal processing unit contains appropriately designed circuits for analyzing the complex rate data which result when two or more reactive species present in the analytical sample will simultaneously react with the substrate coating at distinctly differentiable rates. Rate curves reflecting such situations will usually comprise successive near-straight sections of decreasing slopes separated by curved sections. The respective developments, positions and slopes of said portions are recorded by the signal processing unit and computed to provide results in terms of relative concentrations in the sample of said reactive species.

The following Examples illustrate the invention:

SPECIFIC EXAMPLES

Example 1

To measure the concentration of rabbit antibodies raised against human IgG.

Remark: In the following Example, the reader must be made aware of the following point: In the full preceeding specification, it has been arbitrarily assumed that the known moiety of the complex the formation of which constitutes the basis of the present method is defined as the antibody, the antigen being the conjugate moiety of said complex. It is self-evident that this definition is purely conventional in relation to the present invention. Indeed, in the present Example, the known portion of the complex to be formed is the antigen and the portion to be determined is the antibody.

For this Example, an installation such as that pictured in FIG. 6 was used together with the cell embodiment described with reference to FIG. 7, i.e. a square faced cell of glass (wall about 15 mm wide and 150μ thick, content: 3 ml) and a square glass plate (150μ thick) of about 10 mm placed roughly as the diagonal of the cell. The cell and the plate were first washed in a 2% aqueous detergent solution (RBS) then washed under running water after which they were left overnight in concentrated $H_2SO_4$, then rinsed with distilled water and dried. From this point on, the surfaces subjected to the reflective tests were not touched any more with the fingers.

The plate was then dipped for at least 2 hrs into a 2 g/l solution of human IgG in 0.1 mol/l phosphate buffer. The plate was rinsed with distilled water but not dried immediately before use. Then the plate was immersed into the cuvette and oriented as mentioned above, the cuvette containing 1 ml of the 0.1 mol/l phosphate buffer.

The optical components were adjusted as follows: first the analyzer 3 was adjusted at an angle of 45° relative to the plane of incidence, then the lamp 1, the sample 4 and the detector 8 were positioned for maximal output. The analyzer 7 and the phase plate 6 were rotated for minimal output. This step was repeated adjusting alternately the plate 6 and the analyzer 7 until minimal output was achieved at the lowest possible sensitivity setting on the lock-in amplifier 9. The recorder 10 was switched on and a blank curve was run about 5 min to check stability.

Then 100 μl of test solution (diluted rabbit antihuman IgG) was added to the cuvette and mixing was assured by rapidly bubbling air from a syringe, taking care not to disturb any of the key optical components. The output of the lock-in amplifier was then recorded on the chart display 10 for about 10 min without touching any of the settings previously adjusted. Since for the first minute of recording the trace was irregular due to the effect of bubbles in the reaction medium, the portion of the curve from the end of the first minute to the end of the sixth minute was taken as indicative of the reaction of the antibody with the antigen coated to the plate.

A series of such measurements were made with different concentrations of antibody in the test solution. These concentrations are given in the following Table together with the rate data obtained which constituted the standard rate data which were automatically averaged and stored in the memory of the computer 11.

TABLE

| Experiment No | Concentration of anti-IgG (μg/ml) | Rate data (units/min) |
| --- | --- | --- |
| 1a | 0.827 | 2.38 |
| 1b | 0.827 | 2.34 |
| 2a | 0.568 | 1.40 |
| 2b | 0.568 | 1.47 |
| 3a | 0.350 | 0.91 |
| 3b | 0.350 | 0.784 |
| 4a | 0.178 | 0.24 |
| 4b | 0.178 | 0.268 |
| 5a | 0.09 | 0.084 |
| 5c | 0.09 | 0.074 |

Using the above data as reference data, experiments with unknown concentration of anti-IgG were performed similarly, the rate data found being used for determining said unknown concentration by comparison.

EXAMPLE 2

The method described in Example 1 was repeated but using instead of plate 13 as in FIG. 7, the arrangement shown in FIG. 9 using the same square walled cell and a glass prism with a front angle of 90° and attached to the external cell wall with a suitable index matching fluid of the type used in microscopy techniques. The cuvette inside walls were activated with the antigen as described for the plate in Example 1, after which the experiment was performed by setting the cuvette in the proper position for optimal optical results, adjusting the optical components like in Example 1, adding to the cuvette 1 ml of buffer solution and adding the test solution with agitation. The rest of the experiment was done as described in Example 1 and several concentrations of antibody were tried. It was found that this arrangement was less sensitive than the arrangement used in Example 1. For instance a concentration of antibody of 9.9 μg/ml gave a rate of about 0.9 unit/min.

I claim:

1. A bioassay method for determining a bioactive substance in a sample by the reaction of said bioactive substance, antigen $A_G$ or antibody $A_B$, with its specific binding partner, antibody $A_B$ or antigen $A_G$, respectively, which comprises contacting with the sample to be determined a transparent dielectric substrate the surface of which is at least partly coated with a film of or containing $A_B$ or $A_G$, respectively distributed on the surface of said transparent dielectric substrate, ellipsometrically measuring the rate of optical change occurring in a beam of light where reflection takes place at the boundary line between substrate surface and film as the result of the reaction of $A_B$ and the $A_G$ of the sample, then correlating the rate data thus obtained with standard rate data from identical rate measurements done with known standard samples of $A_G$ or $A_B$, respectively.

2. The method of claim 1, wherein the substrate is a thin dielectric plate and the ellipsometrically measured changes involve elliptically polarized light reflected from the front and the rear-side of the substrate.

3. The method of claim 1, wherein the substrate is a thin dielectric plate and the measured changes involve elliptically polarized light emerging from the plate after multiple reflections therein.

4. A method for determining a bioactive substance in a sample comprising the following steps:
   a. Coating at least part of the surface of a flat dielectric substrate with a film of or containing a specific binding partner of the substance to be determined,
   b. Directing a beam of plane polarized light onto said film coated substrate in a direction and with an angle such that the emerging light is elliptically polarized by its interaction with the said film coated substrate,
   c. Arranging and adjusting optical means in the path of the emerging beam for having the out of phase right-angle directed light vector components of the elliptically polarized light phased in again and the vector sum thereof extinguished to a signal of minimal value,
   d. Contacting with said film coated substrate a solution of the substance to be determined,
   e. Measuring and recording with time the variation of said signal, and
   f. Correlating the rate data thus obtained with standard rate data from identical reactions run with standard samples of known concentration and performing the desired determination by comparison.

5. The method of claim 4, which comprises orienting said substrate relative to the incident beam for enabling the simultaneous collection of the beams of elliptically polarized light externally and internally reflected by the substrate.

6. The method of claim 4, which comprises orienting said substrate relative to the incident beam for causing said beam to undergo multiple reflections within the substrate before emerging from said substrate.

* * * * *